United States Patent
Yangdai (10) Patent No.: US 11,074,721 B2
(45) Date of Patent: *Jul. 27, 2021

(54) METHOD FOR MEASURING OBJECTS IN DIGESTIVE TRACT BASED ON IMAGING SYSTEM

(71) Applicant: ANKON TECHNOLOGIES CO., LTD, Wuhan (CN)

(72) Inventor: Tianyi Yangdai, Wuhan (CN)

(73) Assignee: ANKON TECHNOLOGIES CO., LTD, Wuhan (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/859,784

(22) Filed: Apr. 27, 2020

(65) Prior Publication Data

US 2020/0342628 A1    Oct. 29, 2020

(30) Foreign Application Priority Data

Apr. 28, 2019   (CN) .......................... 201910347966.5

(51) Int. Cl.
*G06T 7/80*   (2017.01)
*G06T 7/50*   (2017.01)
(Continued)

(52) U.S. Cl.
CPC ............ *G06T 7/80* (2017.01); *A61B 1/00057* (2013.01); *A61B 1/041* (2013.01); *G06T 7/50* (2017.01);
(Continued)

(58) Field of Classification Search
CPC .................................. G06T 7/50; G06T 7/80
See application file for complete search history.

(56) References Cited

U.S. PATENT DOCUMENTS

2008/0091069 A1* 4/2008 Groszmann ............... G06T 7/80
600/117
2012/0253122 A1* 10/2012 Minetoma ............ A61B 1/0653
600/109
(Continued)

FOREIGN PATENT DOCUMENTS

CN      101902961      12/2010
CN      107072498      8/2017

*Primary Examiner* — David N Werner
(74) *Attorney, Agent, or Firm* — Treasure IP Group, LLC (57) ABSTRACT

A method for measuring objects in digestive tract based on an imaging system is provided. The imaging system enters a calibration stage, and obtains a calibration image. A measurement stage enters, and the imaging system places in the digestive tract to capture at least one detection image. The depth distance $z_i$ from each pixel in the detection image to the imaging system is calculated, and it records as a depth image z(x, y). The scale r of each pixel in the detection image is calculated according to the depth image z(x, y). The actual two-dimensional coordinates $S_i'$ of each pixel point in the detection image are calculated by the scale r, and the actual three-dimensional coordinates ($S_i'$, z(x, y)) of each pixel are obtained. The distance between any two pixels in the detection image or the area within any range is calculated.

14 Claims, 4 Drawing Sheets

(51) Int. Cl.
    *A61B 1/00*         (2006.01)
    *A61B 1/04*         (2006.01)

(52) U.S. Cl.
    CPC ............... *G06T 2207/10068* (2013.01); *G06T 2207/30028* (2013.01); *G06T 2207/30092* (2013.01)

(56) References Cited

U.S. PATENT DOCUMENTS

| | | | | |
|---|---|---|---|---|
| 2012/0253204 | A1* | 10/2012 | Ben-Yehuda | A61N 5/0603 600/476 |
| 2015/0363932 | A1* | 12/2015 | Hirota | A61B 1/041 382/128 |
| 2016/0217591 | A1* | 7/2016 | Krupnik | G06T 7/62 |
| 2017/0228879 | A1* | 8/2017 | Sato | G01S 17/86 |
| 2018/0042466 | A1* | 2/2018 | Kang | A61B 1/00193 |
| 2018/0047165 | A1* | 2/2018 | Sato | A61B 1/00032 |
| 2018/0325354 | A1* | 11/2018 | Saito | G06T 7/35 |
| 2019/0208986 | A1* | 7/2019 | Saito | A61B 1/00009 |
| 2019/0298154 | A1* | 10/2019 | Mach | G02B 23/24 |
| 2019/0365213 | A1* | 12/2019 | Park | A61B 1/041 |
| 2020/0082510 | A1* | 3/2020 | Wang | H04N 17/002 |
| 2020/0342596 | A1* | 10/2020 | Yangdai | G06T 7/0012 |

* cited by examiner

METHOD FOR MEASURING OBJECTS IN DIGESTIVE TRACT BASED ON IMAGING SYSTEM

CROSS-REFERENCE OF RELATED APPLICATIONS

The application claims priority to Chinese Patent Application No. 201910347966.5 filed on Apr. 28, 2019, the contents of which are incorporated by reference herein.

FIELD OF INVENTION

The present invention relates to image processing, and more particularly to a method for measuring objects in digestive tract based on an imaging system.

BACKGROUND

At present, capsule endoscopes have become increasingly popular for digestive tract examination. Doctors examine subjects through images taken by the capsule endoscopes inside the digestive tract of the subjects. However, for a normal capsule endoscope, when a captured image shows a lesion, the doctor can only determine through the shape, color, position and other characteristics of the lesion, but cannot obtain the size information of the lesion, and therefore cannot give an accurate quantitative analysis result.

In the prior art, for example, according to a Chinese Patent No. CN107072498A, a method for distance measuring in the digestive tract is provided. In the above method, some distance measuring pixels are distributed in a common image sensor to generate distance measuring data for object depth information, that is depth image. Then, the distance measuring data of known pixel positions is used to interpolate the depth of the pixel position of the distance measuring data not derived in the depth image. In the above method, the calculation method is complicated, and the requirements on components are high. The distance measuring pixels need to be evenly distributed in the image sensor, and more measurement points are required. If there are a plurality of measurement points, a large deviation can appear in subsequent gradient calculations, which can eventually cause measurement distortion.

According to a Chinese Patent No. CN101902961A, a device, system and method for estimating the size of an object in a body lumen is provided. In the above method, a laser device is configured in the capsule endoscope, and distance measurement and object measurement are performed by laser points and image brightness. However, the effect of media in the digestive tract is ignored in the method. The environment of the digestive tract is complex. Both air and digestive fluid can affect the optical path of laser and directly affect the result of laser distance measuring. In addition, the distance measurement can always depend on the results of laser distance measuring. Each measurement requires laser distance measuring, and a plurality of calculations are required at each time of measurement, which consumes manpower and material resources.

Therefore, it is necessary to design a new method for measuring objects in the digestive tract.

SUMMARY OF THE INVENTION

To solve one of the above problems, the present invention provides a method for measuring objects in digestive tract based on an imaging system, comprising: simulating an environment of the digestive tract and entering a calibration stage of the imaging system;

controlling the imaging system to photograph at different positions to obtain a calibration image;

calculating and determining the relationship between the brightness co of any pixel in the calibration image and the depth distance z from the actual position of the pixel in the simulated digestive tract to the imaging system, and recording it as:

$$z(x,y)=g(\varphi(x,y)) \quad (1);$$

calculating and determining the relationship between the scale r of any pixel in the calibration image and the depth distance z from the actual position of the pixel in the simulated digestive tract to the imaging system, wherein scale is the actual length represented by unit pixel in the calibration image, and recording it as:

$$r=dz \quad (2);$$

entering a measurement stage after calibration is completed;

placing the imaging system in the digestive tract;

capturing and obtaining at least one detection image;

obtaining the brightness of each pixel in the detection image;

calculating the depth distance $z_i$ from each pixel in the detection image to the imaging system according to equation 1, and recording it as a depth image $z(x, y)$; calculating the scale r of each pixel in the detection image according to equation 2 and the depth image $z(x, y)$;

obtaining the pixel coordinates $S_i$ of each pixel point in the detection image, and calculating the actual two-dimensional coordinates $S_i'$ of each pixel point in the detection image by the scale r;

integrating to obtain the actual three-dimensional coordinates $(S_i', z(x, y))$ of each pixel;

calculating or measuring the distance between any two pixels in the detection image or the area within any range.

In an embodiment, the step "capturing and obtaining at least one detection image" further comprises:

obtaining at least one reference point P in at least one detection image, and recording the actual position of the reference point P in the digestive tract as a target point P'; and wherein the step "calculating the depth distance $z_i$ from each pixel in the detection image to the imaging system according to equation 1" further comprises:

calculating the pixel coordinates $P_i$ of the reference point P separately;

calculating the depth distance $z_i$ from the target point P' to the imaging system separately;

obtaining the predicted brightness $g^{-1}(z_i)$ of the reference point P in the detection image according to equation 1 and the depth distance $z_i$;

comparing the predicted brightness $g^{-1}(z_i)$ of the reference point P with the actual pixel brightness $img(P_i)$ of the reference point P to obtain a correction factor $k_i$, and recording it as:

$$k_i = \frac{g^{-1}(z_i)}{img(P_i)}; \quad (3)$$

obtaining the mean value $\bar{k}$ of the correction factors $k_i$ of all reference points P; calibrating the pixels in the detection image with the mean value $\bar{k}$ of correction factors to obtain the depth distance from each pixel to the imaging system, and recording it as the depth image $z(x, y)$, where:

$$z(x,y)=g(\bar{k}img(x,y)) \quad (4).$$

In an embodiment, the digestive tract comprises a plurality of regions and the imaging system comprises a plurality of exposure levels; and wherein, after the step "obtaining the mean value $\bar{k}$ of the correction factors $k_i$ of all reference points P", the mean value $\bar{k}$ of the correction factors is stored according to different exposure levels and different digestive tract regions.

In an embodiment, after two or more mean values $\bar{k}$ of correction factors are obtained at the same exposure level and digestive tract region, the average of the mean values $\bar{k}$ of correction factors is calculated before storing and updating.

In an embodiment, the step "obtaining at least one reference point P in at least one detection image" comprises:
  obtaining a light spot formed in a detection image;
  calculating the center of the light spot, and recording the center of the light spot as a reference point P, and recording the pixel distance from the reference point P to the image center of the detection image as a reference distance $\Delta p$.

In one embodiment, the calibration stage further comprises:
  obtaining a light spot in the simulated digestive tract;
  calculating the center of the light spot and recording the center as a calibration point Q';
  obtaining a light spot in the calibration image;
  calculating the center of the light spot, and recording the center of the light spot as an imaging point Q, and recording the pixel distance from the imaging point Q to the image center of the calibration image as a reference distance q;
  calculating the relationship between the depth distance z from the calibration point Q' to the imaging system and the reference distance $\Delta q$, and recording it as:

$$z = \frac{a}{\Delta q + b}. \quad (5)$$

In an embodiment, the step "calculating the relationship between the depth distance z from the calibration point Q' to the imaging system and the reference distance $\Delta q$" comprises:
  placing a camera of the imaging system in air or in liquid in the simulated digestive tract, and measuring the depth distance z and reference distance $\Delta q$, and calculating by the equation 5 to obtain the parameter $(a_a, b_a)$ when the camera is in air, and to obtain the parameter $(a_b, b_b)$ when the camera in liquid in the simulated digestive tract.

In an embodiment, in measurement stage, the step "calculating the depth distance $z_i$ from the target point P' to the imaging system separately" comprises:
  obtaining the reference distance $\Delta p$ from the reference point P to the image center of the detection image;
  determining whether the detection image is taken in air or in digestive liquid; when the detection image is taken in air, selecting the parameter $(a_a, b_a)$, and putting it together with the reference distance $\Delta p$ into the equation 5 to calculate the depth distance $z_i$ from the target point P' to the imaging system;
  when the detection image is taken in digestive liquid, selecting the parameter $(a_b, b_b)$, and putting it together with the reference distance $\Delta p$ into the equation 5 to calculate the depth distance $z_i$ from the target point P' to the imaging system.

In one embodiment, the imaging system comprises a plurality of exposure levels, and the calibration stage further comprises:
  determining the relationship between the depth distance z from the calibration point Q' to the imaging system and the exposure levels; and
  wherein the step "determining whether the detection image is taken in air or in digestive liquid" further comprises:
    when $0<\Delta p<q_1$, determining that the detection image is taken in air, and $q_1$ is the value of the air boundary point;
    when $q_1 \leq \Delta p \leq q_2$, comparing the exposure level of the detection image with the exposure level in the calibration stage to determine whether the detection image is taken in air or in digestive liquid, where $q_2$ is the identifiable boundary point value;
    when $q_2<\Delta p$, determining whether the detection image has mucus reflection on the surface of the mucous membrane of digestive tract, and when the detection image has mucus reflection, determining that the image is taken in air, and when the detection image does not have mucus reflection, determining that the image is taken in digestive liquid.

In an embodiment, the step "calculating the depth distance $z_i$ from the target point P' to the imaging system separately" comprises:
  obtaining the time difference t between light emission and light reception; calculating the depth distance $z_i$ from the target point P' to the imaging system, and recording it as:

$$z_i = \tfrac{1}{2}ct\ c \quad (6);$$

where, c represents light speed.

In an embodiment, the step "capturing and obtaining at least one detection image" comprises:
  controlling the imaging system to capture and obtain at least one image;
  correcting the radial distortion of the captured image and forming a detection image, and recording it as:

$$\mathrm{img\_out}(x,y)=\mathrm{img\_in}(x(1+l_1R^2+l_2R^4), y(1+l_1R^2+l_2R^4)) \quad (7);$$

where, $R=\sqrt{x^2+y^2}$ represents the pixel distance from the pixel to the image center of the detection image, $l_1$ and $l_2$ represent distortion parameters of the camera, x represents x-coordinate of the pixel, y represents y-coordinate of the pixel, img_in represents input image, and img_out represents corrected image.

In an embodiment, the step "controlling the imaging system to capture and obtain at least one image" comprises:
  controlling the imaging system to take a first captured image with reference point P;
  controlling the imaging system to take a second captured image without reference point P;
  determining the consistency of the first captured image and the second captured image;
  when it is determined that the first captured image and the second captured image are inconsistent, taking images again;
  when it is determined that the first captured image and the second captured image are consistent, outputting both the first captured image and the second captured image as captured image.

In an embodiment, the step "correcting the radial distortion of the captured image and forming a detection image" comprises:

correcting the radial distortion of the first captured image and forming a first detection image;

correcting the radial distortion of the second captured image and forming a second detection image; and wherein the reference point P is obtained from the first detection image; the depth image z(x, y) is obtained after the second detection image is calibrated.

In an embodiment, the step "determining the consistency of the first captured image and the second captured image" comprises:

adding a mask to the first captured image to completely cover the area of the light spot;

adding a same mask to the second captured image;

comparing the first captured image and the second captured image after adding the mask, and calculating the differentiation index MSE; wherein when MSE≤T, the first captured image and the second captured image are considered to be consistent; and when MSE≥T, the first captured image and the second captured image are considered to be inconsistent.

In an embodiment, the step "calculating the distance between any two pixels in the image or the area within any range" is followed by:

calculating a straight-line distance between any two pixels selected by a user from the detection image according to the three-dimensional coordinates of the two pixels; or, building a three-dimensional image of any area according to the three-dimensional coordinates of pixels in the area selected by a user from the detection image, and calculating a straight-line distance between any two pixels selected by the user from the three-dimensional image; or, calculating the area of any area selected by a user from the detection image according to the three-dimensional coordinates of the area; or, forming a scale on the detection image, and marking graduations on the scale as those of actual length; or, identifying the lesion area in the detection image automatically, and calculating the size or area of the area.

The present invention further provides a measuring system for objects in digestive tract based on an imaging system, comprising:

a size measurement module, configured to measure the depth distance z from an actual position of a pixel in a calibration image in simulated digestive tract to the imaging system, and the scale r of any pixel in the calibration image;

a brightness detection module, configured to identify the brightness of any pixels in the calibration image or a detection image;

a calibration calculation module, configured to calculate the relationship between the brightness φ of any pixel in the calibration image and the depth distance z from the actual position of the pixel in the simulated digestive tract to the imaging system, and record it as equation 1, and to calculate and determine the relationship between the scale r of any pixel in the calibration image and the depth distance z from the actual position of the pixel in the simulated digestive tract to the imaging system, and record it as equation 2;

a measurement and calculation module, configured to obtain the equation 1 of the calibration calculation module and the pixel brightness in the brightness detection module to calculate the depth image z(x, y) of the detection image; and to obtain the equation 2 of the calibration calculation module and the depth image z(x, y) to calculate the actual two-dimensional coordinates $S_i'$ of each pixel in the detection image, and integrate to obtain the actual three-dimensional coordinates $(S_i', z(x, y))$ of each pixel.

Compared to the prior art, in the method described above, the relationship between the brightness φ of any pixel in the calibration image and the depth distance z from the actual position of the pixel in the simulated digestive tract to the imaging system, and the relationship between the scale r of any pixel in the calibration image and the depth distance z from the actual position of the pixel in the simulated digestive tract to the imaging system are obtained first in the calibration stage. Then, in the actual measurement stage, the brightness of each pixel point in the detection image can be obtained to calculate the depth image z(x, y) by the equation 1; further, the scale r of each pixel point can be calculated; the actual two-dimensional coordinates Si' of each pixel point in the detection image can be obtained through the scale r; further, the actual three-dimensional coordinates (Si', z(x, y)) of each pixel point can be obtained by integration. Therefore, through the above method, each imaging system or capsule endoscope can be calibrated in the calibration stage, so that different parameters of the imaging system can be obtained in the process of calibration, and the parameters are needed for measurement and calculation in the subsequent process, so as to avoid errors due to differences in equipment.

DETAILED DESCRIPTION

In order to enable those skilled in the art to better understand the technical solutions disclosed, the present invention can be described in detail below with reference to the accompanying drawings and preferred embodiments. However, the embodiments are not intended to limit the invention, and obviously, the described embodiments are only a part of the embodiments of the present invention, but not all of them. All other embodiments obtained by those having ordinary skill in the art without creative work based on the embodiments of the present invention are included in the scope of the present invention.

Referring to FIGS. 1-4, the present invention provides a method for measuring objects in digestive tract based on a imaging system, where the imaging system can be introduced into the digestive tract to take images of the objects therein, and a two-axis coordinate system is preset on the images taken by the imaging system to determine the coordinates of any pixel in the images. In the embodiment, the imaging system is a capsule endoscope. The capsule endoscope is usually capsule-shaped, and comprises a transparent front shell that encloses an inner board on which the imaging system is disposed, so that the imaging system can take images through the front shell.

In other embodiment, the object of the present invention can also be achieved if the imaging system is other equipment.

For ease of illustration, the following parameters are first described. A calibration point Q' is a position on the photographed object in a calibration stage. An imaging point Q is the corresponding position of the calibration point Q' on a calibration image in the calibration stage. A target point P' is a position on the photographed object in a detection stage. A reference point P is the corresponding position of the target point P' on a detection image in the detection stage.

Specifically, the measurement method comprises the following steps:

simulating the environment of the digestive tract and entering the calibration stage of the imaging system;

controlling the imaging system to photograph at different positions to obtain calibration images;

calculating and determining the relationship between the brightness φ of any pixel in the calibration image and the depth distance z from the actual position of the pixel in the simulated digestive tract to the imaging system, and recording it as:

$$z(x,y)=g(\varphi(x,y)) \qquad (1);$$

calculating and determining the relationship between the scale r of any pixel in the calibration image and the depth distance z from the actual position of the pixel in the simulated digestive tract to the imaging system, where scale is the actual length represented by unit pixel in the calibration image, and recording it as:

$$r=dz \qquad (2);$$

entering a measurement stage after calibration is completed;

placing the imaging system in the digestive tract;

capturing and obtaining at least one detection image;

obtaining the brightness of each pixel in the detection image;

calculating the depth distance $z_i$ from each pixel in the detection image to the imaging system according to equation 1, and recording it as a depth image z(x, y);

calculating the scale r of each pixel in the detection image according to equation 2 and the depth image z(x, y);

obtaining the pixel coordinate $S_i$ of each pixel point in the detection image, and calculating the actual two-dimensional coordinate $S_i'$ of each pixel point in the detection image by the scale r;

integrating to obtain the actual three-dimensional coordinate ($S_i'$, z(x, y)) of each pixel;

calculating or measuring the distance between any two pixels in the detection image or the area within any range.

In the method described above, the relationship between the brightness φ of any pixel in the calibration image and the depth distance z from the actual position of the pixel in the simulated digestive tract to the imaging system, and the relationship between the scale r of any pixel in the calibration image and the depth distance z from the actual position of the pixel in the simulated digestive tract to the imaging system are obtained first in the calibration stage. Then, in the actual measurement stage, the brightness of each pixel point in the detection image can be obtained to calculate the depth image z(x, y) by the equation 1; further, the scale r of each pixel point can be calculated; the actual two-dimensional coordinates $S_i'$ of each pixel point in the detection image can be obtained through the scale r; further, the actual three-dimensional coordinate ($S_i'$, z(x, y)) of each pixel point can be obtained by integration. Therefore, through the above method, each imaging system or capsule endoscope can be calibrated in the calibration stage, so that different parameters of the imaging system can be obtained in the process of calibration, and the parameters are needed for measurement and calculation in the subsequent process, so as to avoid errors due to differences in equipment.

The step "capturing and obtaining at least one detection image" further comprises: obtaining at least one reference point P in at least one detection image, and recording the actual position of the reference point P in the digestive tract as a target point P'.

The step "calculating the depth distance $z_i$ from each pixel in the detection image to the imaging system according to equation 1" further comprises: calculating the pixel coordinate $P_i$ of the reference point P in the detection image separately;

calculating the depth distance $z_i$ from the target point P' to the imaging system separately;

obtaining the predicted brightness $g^{-1}(z_i)$ of the reference point P in the detection image according to equation 1 and the depth distance $z_i$, where the function $g^{-1}$ is an inverse function of the function g;

comparing the predicted brightness $g^{-1}(z_i)$ of the reference point P with the actual pixel brightness img($P_i$) of the reference point P to obtain a correction factor $k_i$, and recording it as:

$$k_i = \frac{g^{-1}(z_i)}{\text{img}(P_i)}; \qquad (3)$$

obtaining the mean value $\bar{k}$ of the correction factors $k_i$ of all reference points P;

calibrating the pixels in the detection image with the mean value $\bar{k}$ of correction factors to obtain the depth distance from each pixel to the imaging system, and recording it as the depth image z(x, y), where:

$$z(x,y)=g(\bar{k}\text{img}(x,y)) \qquad (4).$$

In the actual measurement stage, calculating the depth distance $z_i$ from the target point P' to the imaging system can measure the predicted brightness $g^{-1}(z_i)$ of the reference point P. Then, comparing the predicted brightness $g^{-1}(z_i)$ of the reference point P with the actual pixel brightness img($P_i$) of the reference point P can obtain the correction factor $k_i$. After obtaining the correction factor $k_i$, calibrating all pixels in the detection image can obtain the brightness of each pixel, so as to obtain the depth distance z(x, y) from each pixel to the imaging system. Therefore, through the above method, the reference point P is obtained in the detection image, and then the correction factor is obtained from the predicted brightness and the actual brightness of the reference point P, so that all pixel points can be corrected, making the measurement more accurate. The details can be described below.

Specifically, the actual pixel brightness img($P_i$) of the reference point P is the brightness of the pixel at point P in the detection image. Since the form of the function g can be related to the reflection coefficient of the object surface, exposure parameters, media environment, number of LEDs, distribution, camera lens performance and the response of camera image sensor, although the relationship between the brightness φ of any pixel in the calibration image and the depth distance z from the actual position of the pixel in the simulated digestive tract to the imaging system is obtained during the calibration stage, when the actual distance $z_i$ and the predicted brightness $g^{-1}(z_i)$ are obtained in subsequent process, it still needs to be compared with the actual pixel brightness of the reference point P to obtain a correction factor $k_i$ to calibrate the actual brightness of other pixels to obtain the depth distance $z(x, y)$ of said other pixels.

In addition, in the final calculation process, two pixels or any area can be selected manually or by a system, and then measured by the system; or, the system provides a scale, and the values are directly read or measured manually.

In the embodiment, the reference point P is obtained by a laser device. The laser device emits a ray of light and forms a light spot on both the image captured by the imaging system and the object being captured. Specifically, in th3 embodiment, a VCSEL chip is used, which can emit a laser light with a wavelength of 850 nm or 940 nm. The divergence angle of laser is very small, is mostly less than 6°, and the luminous power is also very small, mostly is mostly less than 1 mW. The VCSEL chip and a camera are mounted together on the inner board of the capsule endoscope to constitute an imaging system. The geometric relationship between the VCSEL chip and the camera is also determined, and a laser light spot can be formed on the captured image. At least one first distance measuring unit is set, the number of the first distance measuring units usually includes 1 to 4, and they are arranged around the camera. Therefore, at least one laser light spot and the reference point P are also formed.

Figure 4:
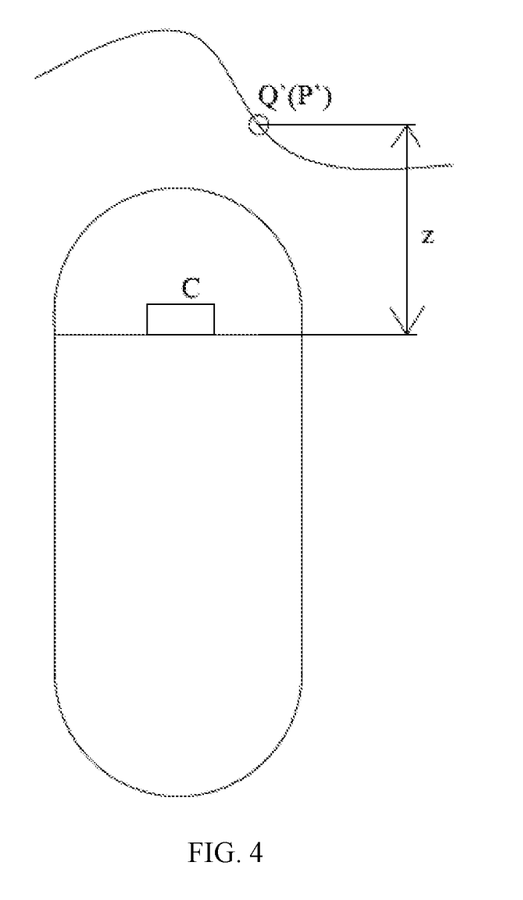
FIG. 4 is a schematic view showing the depth distance z according to the present invention.

Referring to FIG. 4, in the embodiment, when the imaging system C is taking an image, the optical axis of the imaging system is through the center of the image, and the connecting line between the optical axis and the center of the image is recorded as a reference line. Therefore, the depth distance z from the target point P' to the imaging system does not refer to a linear distance between the two, but refers to the distance between the two in line with the direction of the reference line, and the direction of the reference line is the z-axis direction. In addition, the image taken by the imaging system is preset with a two-axis coordinate system recorded as a xoy plane coordinate system. The pixel coordinates $S_i$ and the actual two-dimensional coordinates $S_i'$ of each pixel are based on the xoy plane.

First of all, during calibration, the imaging system needs to be placed in a calibration box. The calibration box is a dark chamber and ensures opacity to light. The calibration box comprises a fixing frame for fixing the imaging system, a target board for the imaging system to take images thereon, and the calibration box is also filled with a simulation medium that can be simulated digestive liquid or air. The imaging system can move on the fixing frame. The imaging system further comprises a plurality of LEDs and a camera, where the LEDs and the camera are both arranged on the inner board of the capsule endoscope, and the number of the LEDs is set to be 2 to 5, and they are distributed around the camera. The light field distribution of the LEDs can affect the distribution of the brightness φ of any pixel in the calibration image, so each different imaging system must be calibrated separately.

Therefore, the imaging system can be set to take images at different positions, under different lighting conditions, in different simulation media and on different target boards to obtain the parameter information. The target board can also be replaced, such as a hard board simulating the mucosal surface or imitating the color of mucosa. When the calibration box is used for other calibrations, only the target board needs to be replaced with a whiteboard, a chess board or a line pairs card, so that white balance correction, camera parameter calibration, resolution measurement and other calibrations can be performed.

Moreover, during calibration, after each image is obtained, a radial distortion correction for the image is required. This is because the capturing of image can be affected by the distortion parameters of different cameras. Therefore, distortion correction can improve the accuracy of size calculation of objects on the image, especially the size measurement of objects at the edge of the image. The image with radial distortion correction can be calibrated to obtain parameter information. The specific information of radial distortion correction can be described in detail later.

In the measurement stage, as the correction factor is obtained, all pixels in the image can be calibrated and the depth distance $z(x, y)$ from each pixel to the imaging system can be obtained. Due to different photographing environments of the imaging system and different positions in the digestive tract, the correction factor can be affected accordingly. Specifically, the digestive tract has a plurality of regions and the imaging system has a plurality of exposure levels according to different photographing environments. So, after the step "obtaining the mean value $\bar{k}$ of the correction factors $k_i$ of all reference points P", the mean value $\bar{k}$ of the correction factors should be stored according to different exposure levels and different digestive tract regions, and updated to a correction factor k. In the same digestive tract region and with the same exposure parameters, the correction factors have small gap, so even if there is no reference point P, the depth distance $z(x, y)$ from each pixel to the imaging system can also be obtained by the above equation 4. This method can not only improve the anti-interference ability of the entire system algorithm, but also reduce the number of images taken with the reference point P, thus improving work efficiency.

If two or more correction factors are obtained at the same exposure level and in the same digestive tract region, the average of the mean values $\bar{k}$ of the correction factors should be calculated before storing and updating. Specifically, as shown in table 1, the digestive tract regions include esophagus, stomach, small intestine, large intestine, etc., the exposure levels include 1, 2 to N, and different exposure levels and digestive tract regions are stored with different correction factor mean values $\bar{k}$. If a new correction factor is added to the table corresponding to the esophagus and level 1 exposure, the original correction factor and the new correction factor are averaged and the average value is stored in the original table. Therefore, if the reference point P is not obtained to calculate the correction factor k, the corresponding correction factor can also be selected for calculation from the table below according to the exposure level and digestive tract region.

TABLE 1

| | Digestive tract regions | | | |
|---|---|---|---|---|
| Exposure levels | Esophagus | Stomach | Small intestine | Large intestine |
| 1 | k11 | k12 | k13 | k14 |
| 2 | k21 | k22 | k23 | k24 |
| ... | ... | ... | ... | ... |
| N | kN1 | kN2 | kN3 | kN4 |

Secondly, as described above, the present invention introduces a laser VCSEL, then the step "obtaining at least one reference point P in at least one detection image" comprises:
obtaining a light spot formed in a detection image;
calculating the center of the light spot, and recording the center of the light spot as a reference point P, and recording the pixel distance from the reference point P to the image center of the detection image as a reference distance Δp.

In the first embodiment of the present invention, the laser is directly used to calculate the depth distance z from the target point P' to the imaging system. The calibration stage further comprises:

obtaining a light spot in the simulated digestive tract;

calculating the center of the light spot and recording the center as a calibration point Q';

obtaining a light spot in the calibration image;

calculating the center of the light spot, and recording the center of the light spot as an imaging point Q, and recording the pixel distance from the imaging point Q to the image center of the calibration image as a reference distance Δq.

Figure 1:
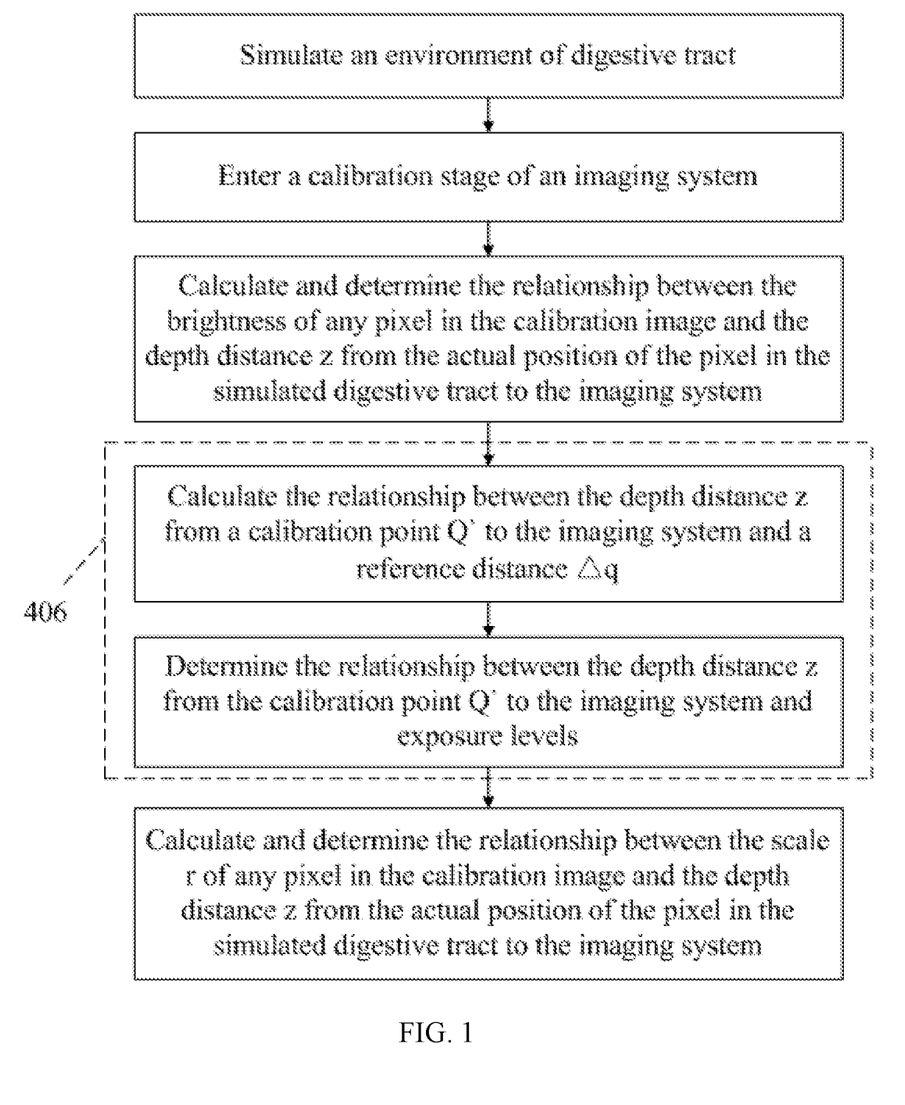
FIG. 1 shows an exemplary flowchart of the measurement method in calibration stage of the present invention.
Figure 2:
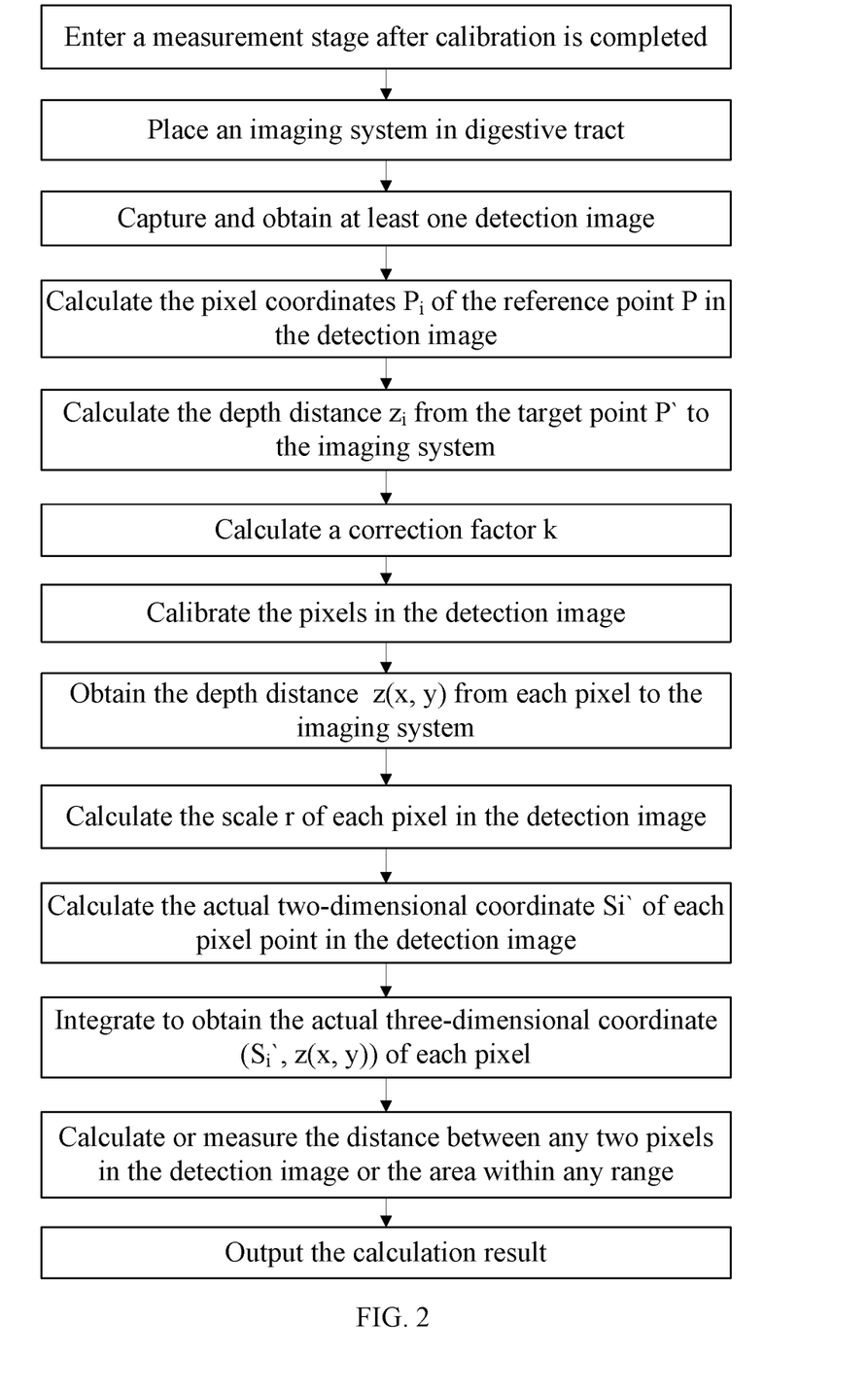
FIG. 2 shows an exemplary flowchart of the measurement method in measurement stage of the present invention.

Therefore, as shown in FIG. 1, in the calibration stage, since the geometric relationship between the laser and the camera is determined, the relationship between the depth distance z from the calibration point Q' to the imaging system and the reference distance Δq from the imaging point Q to the image center of the calibration image can be calibrated. Specifically, the above relationship between the depth distance z from the calibration point Q' to the imaging system and the reference distance Δq is calculated by the following equation:

$$z = \frac{a}{\Delta q + b}. \quad (5)$$

As described above, the environment in digestive tract is complex, for example, the stomach and small intestine are usually water-filled, while the colon, especially from transverse colon to the descending colon, has little water content. The laser passes through the air in the capsule, penetrates the front shell of the capsule, and then enters the digestive tract. Due to the refraction of light, the laser light path can change significantly, resulting in changes in parameters a and b in equation 5. Therefore, specifically, in the calibration stage, the step "calculating the relationship between the depth distance z from the calibration point Q' to the imaging system and the reference distance Δq" comprises: placing the camera in air or in liquid in the simulated digestive tract, and measuring the depth distance z from the calibration point Q' to the imaging system and reference distance Δq from the imaging point Q to the image center of the calibration image, and calculating by the equation 5 to obtain the parameter $(a_a, b_a)$ when the camera is in air and the parameter $(a_b, b_b)$ when the camera in liquid in the simulated digestive tract.

Therefore, in the measurement stage, the step "calculating the depth distance $z_i$ from the target point P' to the imaging system separately" can also be affected by the environment of the digestive tract. Specifically, the above step comprises:

obtaining the reference distance Δp from the reference point P to the image center of the detection image;

determining whether the detection image is taken in air or in digestive liquid; when the detection image is taken in air, selecting the parameter $(a_a, b_a)$, and putting it together with the above reference distance Δp into the equation 5 to calculate the depth distance $z_i$ from the target point P' to the imaging system; when the detection image is taken in digestive liquid, selecting the parameter $(a_b, b_b)$, and putting it together with the above reference distance Δp into the equation 5 to calculate the depth distance $z_i$ from the target point P' to the imaging system. Therefore, the depth distance $z_i$ from the target point P' to the imaging system can be obtained.

According to the above, "determining whether the detection image is taken in air or in digestive liquid" is particularly important. However, the exposure levels should be introduced for determination. Therefore, in the calibration stage, it is also needed to determine the relationship between the depth distance z from the calibration point Q' to the imaging system and the exposure levels. Referring to FIG. 1, the process in the dashed box 406 is an additional calibration process when the first distance measuring unit is used. When the first distance measuring unit is not used, the process in the dashed box 406 may be omitted.

Figure 3:
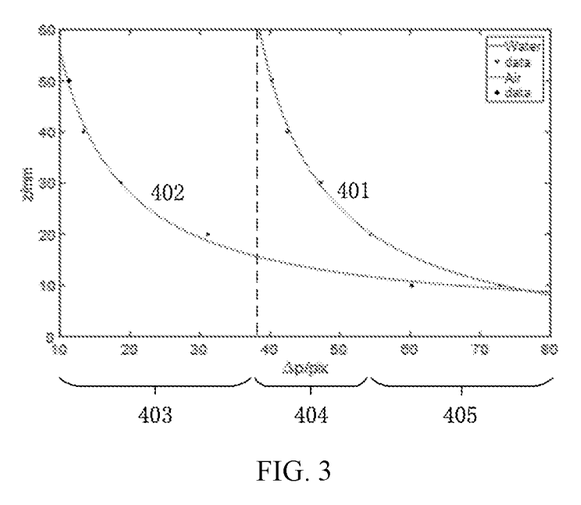
FIG. 3 is a schematic view showing the functional relationship between the depth distance z from the target point P' to the imaging system and the reference distance ΔP from the reference point P to the center of the image according to the present invention.

Specifically, as shown in FIG. 3, the depth distance z from the target point P' to the imaging system and the reference distance Δp from the reference point P to the image center of the detection image have a certain functional relationship, where curve 401 represents the relationship when the environment is digestive liquid, and the curve 402 represents the relationship when the environment is air.

Therefore, according to FIG. 3, the above determination process comprises:

when $0<\Delta p<q_1$, it is determined that the detection image is taken in air, where $q_1$ is the separation point between 403 and 404, i.e the air boundary point. When Δp can be within this range, the detection image must be taken in air.

When $q_1<\Delta p<q_2$, within this range, the exposure levels for taking image in air and in digestive liquid have significant difference. At this point, putting Δp and $(a_a, b_a)$ and $(a_b, b_b)$ into the equation 5 to obtain different $z_i$ values, then determining two exposure levels according to the relationship between the depth distance z and the exposure levels in the calibration stage, and finally comparing them with the actual exposure levels of the detection image to determine whether the detection image is taken in air or simulated digestive liquid; in particular, when the $z_i$ value of one of the two exposure levels is exactly twice that of the other, $\Delta p = q_2$, and $q_2$ is the separation point between 404 and 405, that is the identifiable boundary point value.

When $q_2<\Delta p$, determining whether the detection image has mucus reflection on the surface of the mucous membrane of digestive tract, and when the detection image has mucus reflection, determining that the image is taken in air, and when the detection image does not have mucus reflection, determining that the image is taken in digestive liquid.

Therefore, in the first embodiment, the relationship between the depth distance z from the calibration point Q' to the imaging system and the pixel distance Δq from the imaging point Q to the image center of the calibration image, and the relationship between the depth distance z from the reference point to the imaging system and the exposure levels are required to be calibrated in advance in the calibration stage. Then in the measurement stage, after obtaining the detection image, first obtaining the coordinates $P_i$ of the reference point P, and then obtaining the reference distance Δp from the reference point P to the image center of the detection image, and then determining whether the detection image is taken in air or in digestive liquid; after determining and obtaining the exact parameters $(a_a, b_a)$ or $(a_b, b_b)$, the depth distance $z_i$ from the target point P' in the detection image to the imaging system can be obtained by equation 5.

In the second embodiment of the present invention, the step "calculating the depth distance $z_i$ from the target point P' to the imaging system separately" comprises:

obtaining the time difference t between light emission and light reception; calculating the depth distance $z_i$ from the target point P' to the imaging system, and recording it as:

$$z_i = \tfrac{1}{2}ct \quad (6);$$

where, c represents light speed.

In the embodiment, the imaging system comprises a distance measuring unit that emits light, and the light can be reflected by an obstacle when encountered and received by the distance measuring unit. The distance measuring unit is a time of flight (ToF) chip, and the distance measuring unit can obtain the depth distance $z_i$ from the target point P' to the imaging system directly by the time difference t between light emission and light reception.

Light travels fast in both digestive liquid and air, so the gap caused by the medium in digestive tract is negligible. In the embodiment, a ToF chip is used as the distance measuring unit. Although the ToF chip can directly obtain the depth distance $z_i$ from the target point P' to the imaging system by a relatively simple calculation, the ToF chip is also big in size, so use of the ToF chip in capsule endoscope, such a miniaturized device, is limited.

Moreover, usually, the ToF chip also needs the laser device, i.e VCSEL chip as a light source to form a light spot on the detection image, that is, the laser device is needed to obtain the pixel coordinates $P_i$ of the reference point P in the detection image, and the depth distance $z_i$ from the target point P' to the imaging system can be measured by a second distance measuring unit. In the second embodiment, similarly, the number of the distance measuring units is set as at least 1, usually including 1 to 4, and they are arranged around the camera. Therefore, at least one reference point P is also formed.

Therefore, according to the above, after obtaining the depth distance $z_i$ from a plurality of reference points P and their actual target points P' to the imaging system, the actual two-dimensional coordinates $S_i'$ of each pixel in an xoy plane can be obtained through subsequent calculation of correction factors, scale, etc., and the actual three-dimensional coordinates $(S_i', z(x, y))$ of each pixel can be obtained by integrating the corresponding depth distance $z(x, y)$.

As described above, during calibration, to ensure image accuracy, after each image is obtained, a radial distortion correction for the image is required. Therefore, in the specific implementation process of the present invention, a radial distortion correction is also required for the captured images. Specifically, the step "capturing and obtaining at least one detection image" comprises:

controlling the imaging system to capture and obtain at least one image; correcting the radial distortion of the captured image and forming a detection image, and recording it as:

$$\text{img\_out}(x,y) = \text{img\_in}(x(1+l_1R^2+l_2R^4), y(1+l_1R^2+l_2R^4))c \quad (7);$$

where, $R = \sqrt{x^2+y^2}$ represents the pixel distance from the pixel to the image center of the detection image, $l_1$ and $l_2$ represent distortion parameters of the camera, x represents x-coordinate of the pixel, y represents y-coordinate of the pixel, img_in represents input image, and img_out represents corrected image.

In addition, due to the complex photographing environment, it is very likely that waste films can be produced in the photographing process. Therefore, the captured images should be checked as described below.

Specifically, the step "controlling the imaging system to capture and obtain at least one image" comprises:

controlling the imaging system to take a first captured image with reference point P;

controlling the imaging system to take a second captured image without reference point P;

determining the consistency of the first captured image and the second captured image;

when it is determined that the first captured image and the second captured image are inconsistent, taking images again;

when it is determined that the first captured image and the second captured image are consistent, outputting both the first captured image and the second captured image as captured image;

where, in the actual measurement stage, after entering digestive tract, the imaging system can continuously take two frames of images each time, with an interval of usually less than 40 ms, so the scenes corresponding to the two captured images have only minor change. In addition, the first captured image has a reference point P, so the first captured image is captured with the first or second distance measuring unit turned on, and therefore a light spot is visible; the second captured image is captured with the first distance measuring unit and the second distance measuring unit turned off, so the reference point P does not exist.

Although the scenes corresponding to the first captured image and the second captured image have only minor changes in theory, considering the complex movement conditions in digestive tract, the consistency judgment described above is required.

Specifically, the step "determining the consistency of the first captured image and the second captured image" comprises:

adding a mask to the first captured image to completely cover the area of the light spot;

adding a same mask to the second captured image;

comparing the first captured image and the second captured image after adding the mask, and calculating the differentiation index MSE;

when MSE≤T, the first captured image and the second captured image are considered to be consistent;

when MSE≥T, the first captured image and the second captured image are considered to be inconsistent.

Specifically, how to calculate the differentiation index is not repeated here, and T is a threshold obtained in advance from a plurality of experiments.

In this step, if it is determined that the first captured image and the second captured image are consistent, outputting both the first captured image and the second captured image as captured image. Therefore, in the above radial distortion correction stage, the step "correcting the radial distortion of the captured image and forming a detection image" comprises:

correcting the radial distortion of the first captured image and forming a first detection image;

correcting the radial distortion of the second captured image and forming a second detection image;

where, since a light spot is formed in the first detection image, the pixel coordinates $P_i$ of the reference point P can be obtained by "circle fitting method". Since there is no light spot in the second detection image, lesion information can be completely displayed, so the depth image z(x, y) can be obtained from the second detection image after calibration.

In addition, it is also possible to control the system program to capture only one captured image. At this point, a light spot can also be displayed on the captured image, and subsequent operations can also be performed. However, in this embodiment, by determining the consistency of the first captured image and the second captured image, the accuracy of the detection image and its subsequent calculation can be improved.

Finally, after obtaining the depth image z(x, y) and the actual coordinates $S_i'$ of each pixel in the xoy plane, they can be integrated to obtain the actual three-dimensional coordinates ($S_i'$, z(x, y)) of each pixel. Therefore, after the step of "calculating or measuring the distance between any two pixels in the detection image or the area within any range", the calculation can be performed according to different user interaction modes, and if two detection images are obtained, the user interaction is based on the second detection image.

Specifically, in a first interaction mode, a straight-line distance between any two pixels selected by a user from the detection image can be calculated according to the three-dimensional coordinates of the two pixels.

Or, in a second interaction mode, a three-dimensional image of any area can be built according to the three-dimensional coordinates of pixels in the area selected by a user from the detection image, and a straight-line distance between any two pixels selected by the user from the three-dimensional image can be calculated.

Or, in a third interaction mode, the area of any area selected by an user from the detection image can be calculated according to the three-dimensional coordinates of the area.

Or, in a fourth interaction mode, a scale is formed on the detection image, and the graduations on the scale are marked as those of actual length, users can place the scale at different positions, and the graduations of the scale at different positions are also different, then users can read and measure by themselves.

Or, in a fifth interaction mode, the lesion area in the detection image can be automatically identified, with the size or area of the area calculated.

The above step "calculating the distance between any two pixels in the image or the area within any range" is not limited to have only the five interaction modes, but the calculation method is based on that the actual three-dimensional coordinates of each pixel have been obtained, so other interaction modes if any are also within the protection scope of the present invention.

Therefore, the present invention further provides a measuring system for objects in the digestive tract based on an imaging system, comprising:

a size measurement module, configured to measure the depth distance z from the actual position of a pixel in the calibration image in the simulated digestive tract to the imaging system, and the scale r of any pixel in the calibration image; a brightness detection module, configured to identify the brightness of any pixels in the calibration image or detection image;

a calibration calculation module, configured to calculate the relationship between the brightness φ of any pixel in the calibration image and the depth distance z from the actual position of the pixel in the simulated digestive tract to the imaging system, and record it as equation 1, and to calculate and determine the relationship between the scale r of any pixel in the calibration image and the depth distance z from the actual position of the pixel in the simulated digestive tract to the imaging system, and record it as equation 2;

a measurement and calculation module, configured to obtain the equation 1 of the calibration calculation module and the pixel brightness in the brightness detection module to calculate the depth image z(x, y) of the detection image; and to obtain the equation 2 of the calibration calculation module and the depth image z(x, y) to calculate the actual two-dimensional coordinates $S_i'$ of each pixel in the detection image, and integrate to obtain the actual three-dimensional coordinates ($S_i'$, z(x, y)) of each pixel.

In summary, the method for measuring objects in the digestive tract based on the imaging system in the present invention can obtain some parameter information in advance through the calibration stage of the imaging system, and thereby facilitate the calculation in the measurement stage and avoid calculation error caused by equipment difference between imaging systems. Secondly, by the storage of correction factors k, after the storage amount of k is getting larger and the value of k is getting more stable, the correction factor k may not be calculated in the subsequent photographing process, so the use of laser device and distance measuring unit can be reduced. Finally, when a laser device is used, through separate measurement in different digestive tract environments in the calibration stage, the scenes in the digestive tract, air or digestive liquid, can also be determined in the measurement stage, so that different processing methods can be selected to improve accuracy.

It should be understood that, although the specification is described in terms of embodiments, not every embodiment merely comprises an independent technical solution. Those skilled in the art should have the specification as a whole, and the technical solutions in each embodiment may also be combined as appropriate to form other embodiments that can be understood by those skilled in the art.

The present invention by no means is limited to the preferred embodiments described above. On the contrary, many modifications and variations are possible within the scope of the appended claims.

What is claimed is:

1. A method for measuring objects in digestive tract based on an imaging system, comprising:

simulating an environment of the digestive tract and entering a calibration stage of the imaging system;

controlling the imaging system to photograph at different positions to obtain a calibration image;

calculating and determining the relationship between the brightness φ of any pixel in the calibration image and the depth distance z from the actual position of the pixel in the simulated digestive tract to the imaging system, and recording it as:

$$z(x,y)=g(\varphi(x,y)) \quad (1);$$

calculating and determining the relationship between the scale r of any pixel in the calibration image and the depth distance z from the actual position of the pixel in the simulated digestive tract to the imaging system, wherein scale is the actual length represented by unit pixel in the calibration image, and recording it as:

$$r=dz \quad (2);$$

wherein d is a parameter having a constant value determined by lens and image sensor at use in the imaging system, entering a measurement stage after calibration is completed;

placing the imaging system in the digestive tract;

capturing and obtaining at least one detection image;

obtaining the brightness of each pixel in the detection image;

calculating the depth distance $z_i$ from each pixel in the detection image to the imaging system according to equation 1, and recording it as a depth image z(x, y);

calculating the scale r of each pixel in the detection image according to equation 2 and the depth image z(x, y);

obtaining the pixel coordinates $S_i$ of each pixel point in the detection image, and calculating the actual two-dimensional coordinates $S_i'$ of each pixel point in the detection image by the scale r;

integrating to obtain the actual three-dimensional coordinates ($S_i'$, z(x, y)) of each pixel;

calculating or measuring the distance between any two pixels in the detection image or the area within any range, wherein the step "capturing and obtaining at least one detection image" further comprises: obtaining at least one reference point P in at least one detection image, and recording the actual position of the reference point P in the digestive tract as a target point P'; and wherein the step "calculating the depth distance $z_i$ from each pixel in the detection image to the imaging system according to equation 1" further comprises:

calculating the pixel coordinates $P_i$ of the reference point P separately;

calculating the depth distance $z_i$ from the target point P' to the imaging system separately;

obtaining the predicted brightness $g^{-1}(z_i)$ of the reference point P in the detection image according to equation 1 and the depth distance $z_i$;

comparing the predicted brightness $g^{-1}(z_i)$ of the reference point P with the actual pixel brightness img($P_i$) of the reference point P to obtain a correction factor $k_i$, and recording it as:

$$k_i = \frac{g^{-1}(z_i)}{img(P_i)}; \qquad (3)$$

obtaining the mean value $\bar{k}$ of the correction factors $k_i$ of all reference points P;

calibrating the pixels in the detection image with the mean value $\bar{k}$ of correction factors to obtain the depth distance from each pixel to the imaging system, and recording it as the depth image z(x, y), where:

$$z(x,y)=g(\bar{k}img(x,y)) \qquad (4);$$

wherein the step "obtaining at least one reference point P in at least one detection image" comprises:

obtaining a light spot formed in a detection image;

calculating the center of the light spot, and recording the center of the light spot as a reference point P, and recording the pixel distance from the reference point P to the image center of the detection image as a reference distance Δp.

2. The method of claim 1, wherein the digestive tract comprises a plurality of regions and the imaging system comprises a plurality of exposure levels; and wherein, after the step "obtaining the mean value $\bar{k}$ of the correction factors $k_i$ of all reference points P", the mean value $\bar{k}$ of the correction factors is stored according to different exposure levels and different digestive tract regions.

3. The method of claim 2, wherein after two or more mean values $\bar{k}$ of correction factors are obtained at the same exposure level and digestive tract region, calculating the average of the mean values $\bar{k}$ of correction factors before storing and updating.

4. The method of claim 1, wherein the calibration stage further comprises:

obtaining a light spot in the simulated digestive tract;

calculating the center of the light spot and recording the center as a calibration point Q';

obtaining a light spot in the calibration image;

calculating the center of the light spot, and recording the center of the light spot as an imaging point Q, and recording the pixel distance from the imaging point Q to the image center of the calibration image as a reference distance Δq;

calculating the relationship between the depth distance z from the calibration point Q' to the imaging system and the reference distance Δq, and recording it as:

$$z = \frac{a}{\Delta q + b}. \qquad (5)$$

5. The method of claim 4, wherein the step "calculating the relationship between the depth distance z from the calibration point Q' to the imaging system and the reference distance Δq" comprises:

placing a camera of the imaging system in air or in liquid in the simulated digestive tract, and measuring the depth distance z and reference distance Δq, and calculating by the equation 5 to obtain the parameter ($a_a$, $b_a$) when the camera is in air, and to obtain the parameter ($a_b$, $b_b$) when the camera in liquid in the simulated digestive tract.

6. The method of claim 5, wherein in the measurement stage, the step "calculating the depth distance $z_i$ from the target point P' to the imaging system separately" comprises:

obtaining the reference distance Δp from the reference point P to the image center of the detection image;

determining whether the detection image is taken in air or in digestive liquid;

when the detection image is taken in air, selecting the parameter ($a_a$, $b_a$), and putting it together with the reference distance Δp into the equation 5 to calculate the depth distance $z_i$ from the target point P' to the imaging system;

when the detection image is taken in digestive liquid, selecting the parameter ($a_b$, $b_b$), and putting it together with the reference distance Δp into the equation 5 to calculate the depth distance $z_i$ from the target point P' to the imaging system.

7. The method of claim 6, wherein the imaging system comprises a plurality of exposure levels, and the calibration stage further comprises:

determining the relationship between the depth distance z from the calibration point Q' to the imaging system and the exposure levels; and wherein the step "determining whether the detection image is taken in air or in digestive liquid" further comprises:

when 0<Δp<$q_1$, determining that the detection image is taken in air, and $q_1$ is the value of the air boundary point;

when $q_1$≤Δp≤$q_2$, comparing the exposure level of the detection image with the exposure level in the calibration stage to determine whether the detection image is taken in air or in digestive liquid, where $q_2$ is the identifiable boundary point value;

when $q_2$<Δp, determining whether the detection image has mucus reflection on the surface of the mucous membrane of digestive tract, and when the detection image has mucus reflection, determining that the image is taken in air, and when the detection image does not have mucus reflection, determining that the image is taken in digestive liquid.

8. The method of claim 1, wherein the step "calculating the depth distance $z_i$, from the target point P' to the imaging system separately" comprises:
   obtaining the time difference t between light emission and light reception;
   calculating the depth distance $z_i$, from the target point P' to the imaging system, and recording it as:

$$z_i = \tfrac{1}{2} ct \; c \quad (6);$$

where, c represents light speed.

9. The method of claim 1, wherein the step "capturing and obtaining at least one detection image" comprises:
   controlling the imaging system to capture and obtain at least one image;
   correcting the radial distortion of the captured image and forming a detection image, and recording it as:

$$\mathrm{img\_out}(x,y) = \mathrm{img\_in}(x(1+l_1 R^2 + l_2 R^4), y(1+l_1 R^2 + l_2 R^4)) \quad (7);$$

where, $R = \sqrt{x^2+y^2}$ represents the pixel distance from the pixel to the image center of the detection image, $l_1$ and $l_2$ represent distortion parameters of the camera, x represents x-coordinate of the pixel, y represents y-coordinate of the pixel, img_in represents input image, and img_out represents corrected image.

10. The method of claim 9, wherein the step "controlling the imaging system to capture and obtain at least one image" comprises:
    controlling the imaging system to take a first captured image with reference point P;
    controlling the imaging system to take a second captured image without reference point P;
    determining the consistency of the first captured image and the second captured image;
    when it is determined that the first captured image and the second captured image are inconsistent, taking images again;
    when it is determined that the first captured image and the second captured image are consistent, outputting both the first captured image and the second captured image as captured image.

11. The method of claim 10, wherein the step "correcting the radial distortion of the captured image and forming a detection image" comprises:
    correcting the radial distortion of the first captured image and forming a first detection image;
    correcting the radial distortion of the second captured image and forming a second detection image; and
    wherein the reference point P is obtained from the first detection image; the depth image z(x, y) is obtained after the second detection image is calibrated.

12. The method of claim 10, wherein the step "determining the consistency of the first captured image and the second captured image" comprises:
    adding a mask to the first captured image to completely cover the area of the light spot;
    adding a same mask to the second captured image;
    comparing the first captured image and the second captured image after adding the mask, and calculating the differentiation index MSE; wherein
    when MSE≤T, the first captured image and the second captured image are considered to be consistent; and
    when MSE>T, the first captured image and the second captured image are considered to be inconsistent.

13. The method of claim 1, wherein the step "calculating the distance between any two pixels in the detection image or the area within any range" is followed by:
    calculating a straight-line distance between any two pixels selected by a user from the detection image according to the three-dimensional coordinates of the two pixels; or,
    building a three-dimensional image of any area according to the three-dimensional coordinates of pixels in the area selected by a user from the detection image, and calculating a straight-line distance between any two pixels selected by the user from the three-dimensional image; or,
    calculating the area of any area selected by a user from the detection image according to the three-dimensional coordinates of the area; or,
    forming a scale on the detection image, and marking graduations on the scale as those of actual length; or,
    identifying a lesion area in the detection image automatically, and calculating the size or area of the area.

14. A measuring system for objects in digestive tract based on an imaging system, comprising:
    one or more computer processors configured to:
       measure the depth distance z from an actual position of a pixel in a calibration image in simulated digestive tract to the imaging system, and the scale r of any pixel in the calibration image;
       identify the brightness of any pixels in the calibration image or a detection image;
       calculate the relationship between the brightness φ of any pixel in the calibration image and the depth distance z from the actual position of the pixel in the simulated digestive tract to the imaging system, and record it as equation 1, $$z(x,y) = g(\varphi(x,y)) \quad (1);$$

and calculate and determine the relationship between the scale r of any pixel in the calibration image and the depth distance z from the actual position of the pixel in the simulated digestive tract to the imaging system, and record it as equation 2, $$r = dz \quad (2);$$

wherein d is a parameter having a constant value determined by lens and image sensor at use in the imaging system,
       obtain the equation 1 of the calibration calculation module and the pixel brightness in the brightness detection module to calculate the depth image z(x, y) of the detection image; and to obtain the equation 2 of the calibration calculation module and the depth image z(x, y) to calculate the actual two-dimensional coordinates $S_i'$ of each pixel in the detection image, and integrate to obtain the actual three-dimensional coordinates ($S_i'$, z(x, y)) of each pixel,
       wherein the step "identify the brightness of any pixels in the calibration image or a detection image" further comprises:
    obtaining at least one reference point P in at least one detection image, and recording the actual position of the reference point P in the digestive tract as a target point P'; and
       wherein the step "calculate the relationship between the brightness φ of any pixel in the calibration image and the depth distance z from the actual position of the pixel in the simulated digestive tract to the imaging system, and record it as equation 1" further comprises:
       calculating the pixel coordinates $P_i$ of the reference point P separately;

calculating the depth distance $z_i$ from the target point P' to the imaging system separately;

obtaining the predicted brightness $g^{-1}(z_i)$ of the reference point P in the detection image according to equation 1 and the depth distance $z_i$;

comparing the predicted brightness $g^{-1}(z_i)$ of the reference point P with the actual pixel brightness img ($P_i$) of the reference point P to obtain a correction factor $k_i$, and recording it as:

$$k_i = \frac{g^{-1}(z_i)}{\text{img}(P_i)}; \qquad (3)$$

obtaining the mean value $\bar{k}$ of the correction factors $k_i$, of all reference points P;

calibrating the pixels in the detection image with the mean value $\bar{k}$ of correction factors to obtain the depth distance from each pixel to the imaging system, and recording it as the depth image z(x, y), where:

$$z(x,y)=g(\bar{k}\,\text{img}(x,y)) \qquad (4);$$

wherein the step "obtaining at least one reference point P in at least one detection image" comprises:

obtaining a light spot formed in a detection image;

calculating the center of the light spot, and recording the center of the light spot as a reference point P, and recording the pixel distance from the reference point P to the image center of the detection image as a reference distance Δp.

* * * * *